(12) United States Patent
Saravanan et al.

(10) Patent No.: US 11,306,336 B2
(45) Date of Patent: Apr. 19, 2022

(54) PROCESS FOR PRODUCTION OF GALACTO-OLIGOSACCHARIDES

(71) Applicant: Tata Chemicals Limited, Mumbai (IN)

(72) Inventors: R Saravanan, Pune (IN); S Narayanan, Pune (IN); Deepak Jadhav, Pune (IN); Manish Jain, Pune (IN); Shajahan Shubethar, Pune (IN); Shankar Lade, Pune (IN); Manoj Gote, Pune (IN); Ashok Kumar Dubey, Pune (IN)

(73) Assignee: Tata Chemicals Limited, Mumbai (IN)

( * ) Notice: Subject to any disclaimer, the term of this patent is extended or adjusted under 35 U.S.C. 154(b) by 264 days.

(21) Appl. No.: 16/477,629

(22) PCT Filed: Mar. 9, 2018

(86) PCT No.: PCT/IB2018/051549
§ 371 (c)(1),
(2) Date: Jul. 12, 2019

(87) PCT Pub. No.: WO2018/131008
PCT Pub. Date: Jul. 19, 2018

(65) Prior Publication Data
US 2019/0338327 A1    Nov. 7, 2019

(30) Foreign Application Priority Data

Jan. 13, 2017 (IN) .............................. 201721001404

(51) Int. Cl.
*C12P 19/04* (2006.01)
(52) U.S. Cl.
CPC .................................... *C12P 19/04* (2013.01)
(58) Field of Classification Search
CPC ....................................................... C12P 19/04
See application file for complete search history.

(56) References Cited

U.S. PATENT DOCUMENTS

| | | | |
|---|---|---|---|
| 9,139,856 B2 | 9/2015 | Avalakki et al. | |
| 2014/0038269 A1* | 2/2014 | Ikeda | C12N 9/96 435/255.1 |
| 2019/0290675 A1* | 9/2019 | Gibson | A61K 9/0095 |

FOREIGN PATENT DOCUMENTS

IN    253177    10/2008

OTHER PUBLICATIONS

Gorin, P. A. J. et al., "The structures of galactosyl-lactose and galactobiosyl-lactose produced from lactose by Sporobolomyces singularis." Canadian Journal of Chemistry 42.6 (1964): 1341-1344. abstract, p. 1343 "Production of Oligosaccharides":full para and "Isolation of Oligosaccharides": first line.

Sakai, T. et al., "Repeated-batch production of galactooligosaccharides from lactose at high concentration by using alginate-immobilized cells of Sporobolomyces singularis YIT 10047." The Journal of general and applied microbiology 54.5 (2008): 285-293. abstract, Fig. 1, p. 286: right side column, last para—p. 287: left side column. second para.

Cho, Youn-Jeung et al., "Purification and biochemical properties of a galactooligosaccharide producing ?-galactosidase from Bullera singularis."

International Searching Authority, Written Opinion issued in International Application No. PCT/B2018/051549 dated Jun. 20, 2018 (6 pages).

International Searching Authority, Search Report issued in International Application No. PCT/B2018/051549 dated Jun. 20, 2018 (1 page).

* cited by examiner

*Primary Examiner* — Maryam Monshipouri
(74) *Attorney, Agent, or Firm* — Wood Herron & Evans LLP

(57) ABSTRACT

A process for production of galacto-oligosaccharides is provided. The process for production of galacto-oligosaccharides includes growing *Sporobolomyces singularis* in a fermentation medium, harvesting the said microbes from the fermentation medium, inoculating the said microbes with lactose solution in a reactor and incubating in an aerobic condition to convert lactose into galacto-oligosaccharides. The process also includes separating the galacto-oligosaccharides from the microbes; filtering thus obtained galacto-oligosaccharides; and optionally making the powder form of galacto-oligosaccharides. The process for producing galacto-oligosaccharides provides high yield and high purity.

7 Claims, 3 Drawing Sheets

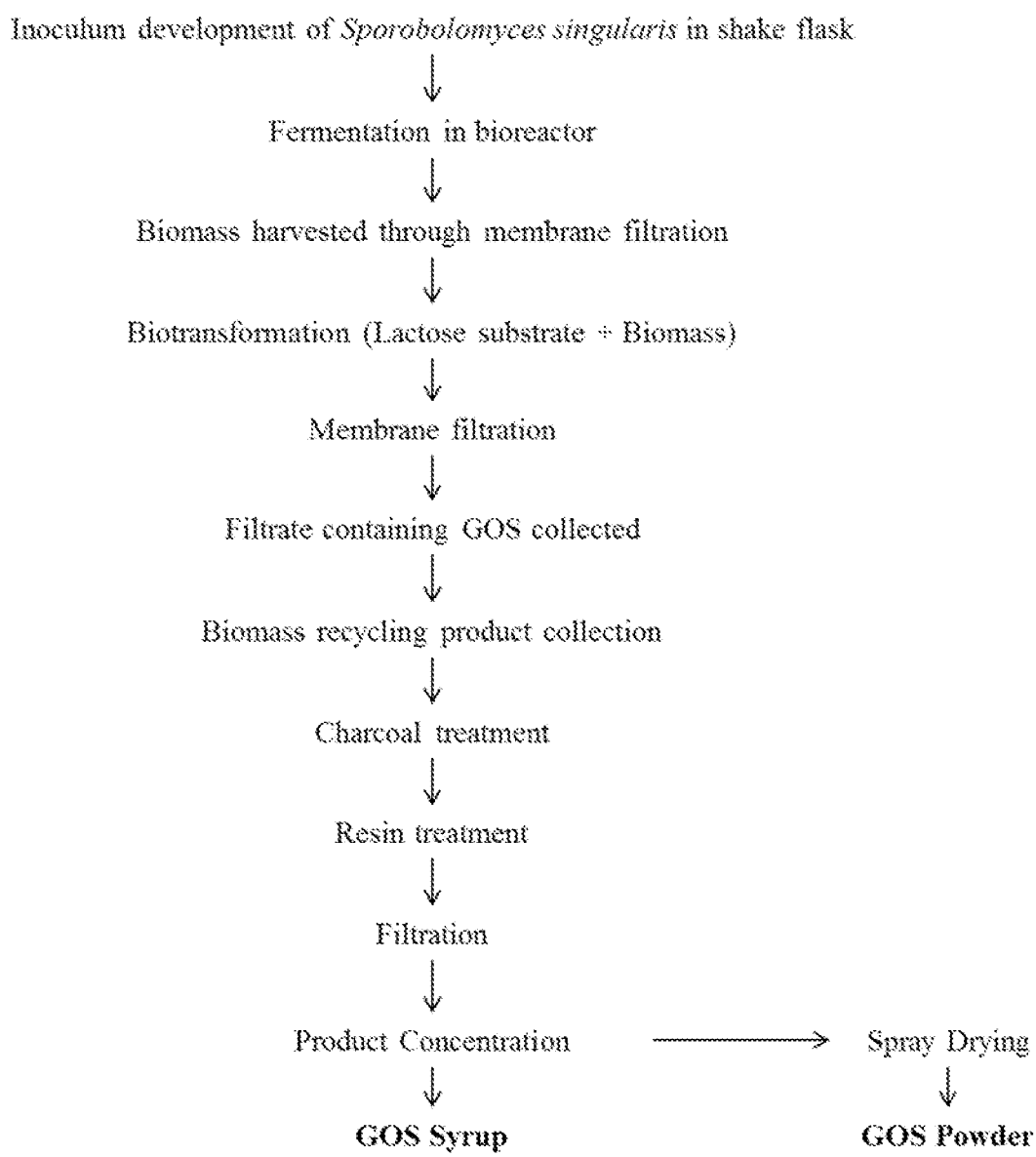
Figure 1: Process flow diagram of producing galacto-oligosaccharides in accordance with an embodiment of the present disclosure

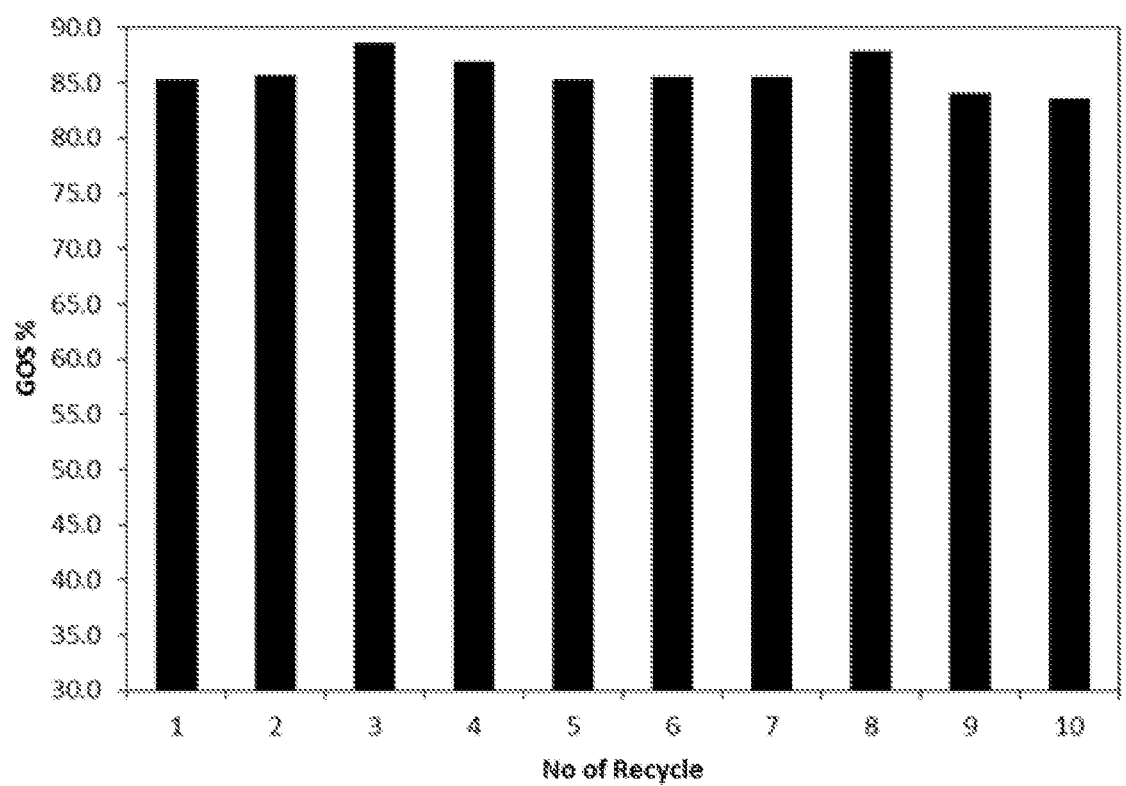
Figure 2: Galacto-oligosaccharides yield data of 10 cycles using the process of the present disclosure

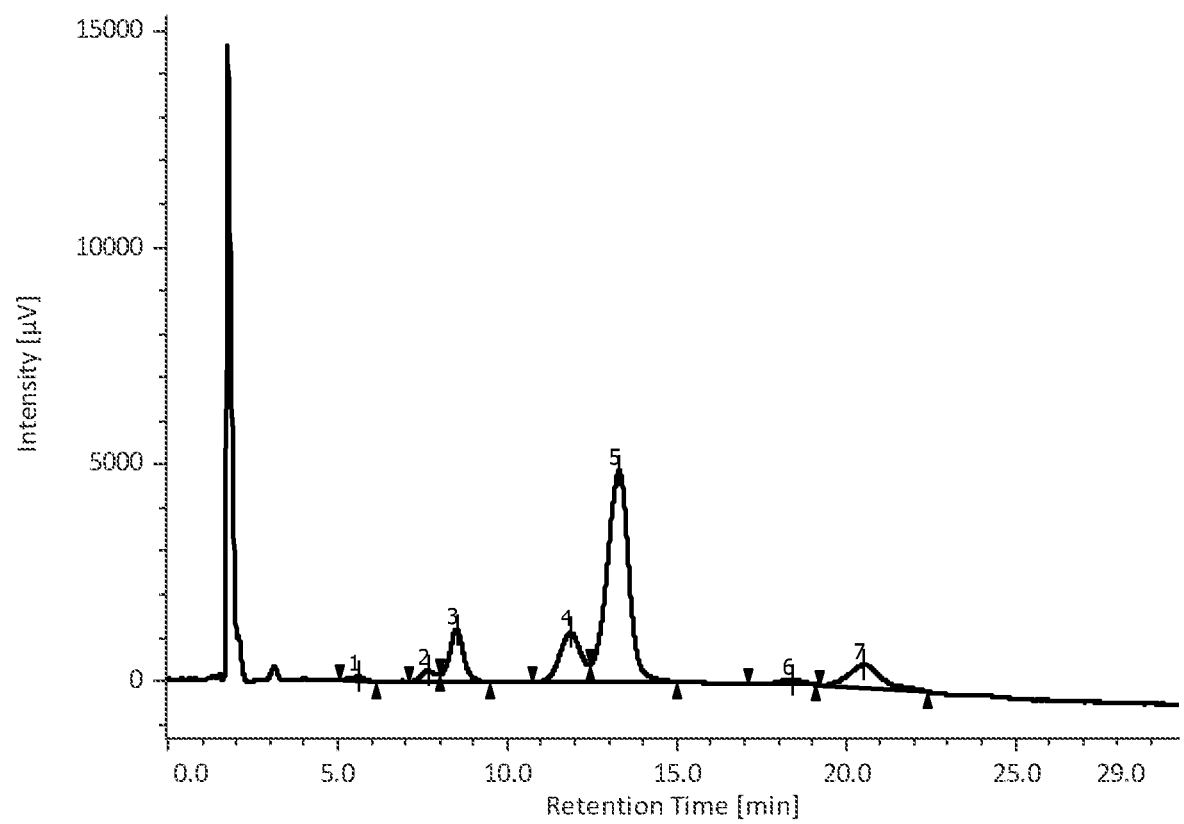
Figure 3: HPLC chromatogram of galacto-oligosaccharides produced using the process of the present disclosure

PROCESS FOR PRODUCTION OF GALACTO-OLIGOSACCHARIDES

CROSS-REFERENCE TO RELATED APPLICATION

This application is a national phase entry of, and claims priority to, International Application No. PCT/IB2018/051549, filed Mar. 9, 2018, which claims priority to Indian Application Number 201721001404, filed Jan. 13, 2017, both with the same title as listed above. The above-mentioned patent applications are incorporated herein by reference in their entireties.

TECHNICAL FIELD

The present invention relates generally to a process for production of a nondigestible oligosaccharide.

BACKGROUND

Galacto-oligosaccharides (GOS) are nondigestible oligosaccharides (prebiotic) and are composed of 2 to 20 molecules of galactose and 1 molecule of glucose at terminal end. Galacto-oligosaccharides have widespread use in yogurt, soft drinks, chewing gums, cookies, ice creams and powdered & clabbered milk industry as prebiotics.

A GOS can be produced by a series of enzymatic reactions catalyzed by β-galactosidase, where the glycosyl group of one or more D-galactosyl units is transferred onto the D-galactose moiety of lactose, in a process known as transgalactosylation and when the acceptor is water, galactose is produced and the process is known as hydrolysis. In the reaction mixture, β-galactosidase can catalyze hydrolysis and the transgalactosylation reaction concurrently, resulting in low yield of GOS. In the case of GOS synthesis, transgalactosyl reaction is desired as opposed to hydrolysis.

The U.S. Pat. No. 9,139,856 discloses a process of using two microbe system to remove the feedback inhibition. However this process is complicated and adds to additional production cost.

A number of processes have been developed for the production of galacto-oligosaccharides using single culture. However the maximum yield reported is only 50% using *Bullera singularis* (Cho and others, 2003).

Therefore, there is a need to develop a simple and cost effective process to produce galacto-oligosaccharides having maximum yield and high purity.

SUMMARY

In one embodiment, a process for producing galacto-oligosaccharides is provided. The process comprises growing *Sporobolomyces singularis* in a fermentation medium, harvesting the microbes from the fermentation medium, inoculating the microbes with lactose solution in a reactor and incubating in an aerobic condition at a temperature in the range of 35 to 40° C., wherein the ratio of the microbes with respect to lactose solution is at least 5% on w/v basis and the microbes are capable of converting at least 80% of lactose into galacto-oligosaccharides; separating the galacto-oligosaccharides from the microbes; filtering the thus obtained galacto-oligosaccharides; and optionally making the powder form of galacto-oligosaccharides.

The process for producing galacto-oligosaccharides provides high yield and high purity.

BRIEF DESCRIPTION OF THE DRAWINGS

FIG. 1 illustrates process flow diagram of producing galacto-oligosaccharides in accordance with an embodiment of the present disclosure.

FIG. 2 shows galacto-oligosaccharides yield data of 10 cycles using the process of the present disclosure.

FIG. 3 shows HPLC chromatogram of galacto-oligosaccharides produced using the process of the present disclosure.

DETAILED DESCRIPTION

For the purpose of promoting an understanding of the principles of the disclosure, reference will now be made to embodiments and specific language will be used to describe the same. It will nevertheless be understood that no limitation of the scope of the disclosure is thereby intended, such alterations and further modifications in the disclosed composition and method, and such further applications of the principles of the disclosure therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof.

Reference throughout this specification to "one embodiment" "an embodiment" or similar language means that a particular feature, structure, or characteristic described in connection with the embodiment is included in at least one embodiment of the present disclosure. Thus, appearances of the phrase "in one embodiment", "in an embodiment" and similar language throughout this specification may, but do not necessarily, all refer to the same embodiment.

The disclosure relates to a process for producing galacto-oligosaccharides. The process comprises growing *Sporobolomyces singularis* in a fermentation medium, harvesting the microbes from the fermentation medium, inoculating the microbes with lactose solution in a reactor and incubating in an aerobic condition at a temperature in the range of 35 to 40° C., wherein the ratio of the microbes w.r.t to lactose solution is at least 5% on w/v basis and the microbes are capable of converting at least 80% of lactose into galacto-oligosaccharides; separating the galacto-oligosaccharides from the microbes; filtering the thus obtained galacto-oligosaccharides and optionally drying to get galacto-oligosaccharides in form of powder.

In accordance with an embodiment of the invention, the microbe is *Sporobolomyces singularis*. In accordance with a preferred aspect, *Sporobolomyces singularis* is *Sporobolomyces singularis* MCC 0096. The *Sporobolomyces singularis* MCC 0096 was deposited on May 10, 2016, at international depositary authority Microbial Culture Collection, National Centre for Cell Science (Sai Trinity Complex, Sus Road, Pashan, Pune-411021, Maharashtra, India), under Accession No. MCC 0096. The deposited material has an identification reference in the depository of TCL-IC-WVT-ID-Y-0002. In accordance with an embodiment, the fermentation medium comprises the nitrogen source including but not limited to yeast extract, peptone, tryptone, beef extract, malt extract, cotton seed meal, urea and a mixture thereof, carbon source includes but not limited to glucose, molasses, dextrose, lactose, maltodextrin and a mixture thereof, buffering agent including sodium, potassium and calcium salts and mixture thereof. The ratio of the various ingredients for fermentation medium is well known in the art and not limited to specific example disclosed herewith. In accordance with an aspect the pH of the fermentation medium ranges from 6 to 7. The pH of the fermentation medium is adjusted using 0.1 N NaOH.

In accordance with an embodiment of the invention, the fermentation medium contains lactose. The concentration of lactose in the fermentation medium ranges from 15 gm/l to 30 gm/l.

In accordance with an aspect, the fermentation is carried out at a temperature range of 25 to 30° C. The temperature of the fermentation medium is measured using temperature probes. In accordance with a preferred aspect of the invention, fermentation is carried out at 27° C. temperature.

In accordance with an embodiment, the fermentation medium contains lactose. The concentration of lactose in the fermentation medium ranges from 15 gm/l to 30 gm/l.

In accordance with an embodiment, the microbes are harvested from fermentation medium using any known methods but not limited to filtration and centrifugation. In accordance with an embodiment the microbes are harvested from fermentation medium when $OD_{620}$ of the medium is in the range of 5 to 6. $OD_{620}$ is an abbreviation indicating the absorbance, or optical density, of a sample measured at a wavelength of 620 nm. In accordance with an alternative embodiment, the microbes are harvested when at least 70% of the lactose has been utilized by the microbes. In accordance with a preferred aspect of the invention, the microbes are harvested when the $OD_{620}$ of the medium reaches in the range of 5 to 6 and at least 70% of the lactose has been utilized by the microbes.

In accordance with an embodiment, the harvested microbes are inoculated in a reactor comprising lactose solution, wherein the ratio of the microbes with respect to lactose solution is at least 5% on w/v basis. In accordance with an aspect, the lactose ranges from 10 to 40% in the lactose solution. In accordance with an aspect, the reactor is bioreactor. In accordance with as aspect, the ratio of the inoculated microbes ranges from the 5 to 10% on w/v basis. In accordance with an aspect, the microbes convert at least 80% of lactose present in the bioreactor into galacto-oligosaccharides at a temperature in the range of 35 to 40° C. In accordance with a preferred embodiment, the microbe convert at least 85% of lactose present in the bioreactor into galacto-oligosaccharides at a temperature in the range of 35 to 40° C. In accordance with a related embodiment, the bioreactor is selected from batch reactor, fed batch reactor and continuous reactor.

In accordance with an embodiment, the biotransformation is carried out for at least 15 hours. In accordance with a preferred embodiment, the biotransformation is carried for the time in the range of 15 to 25 hours. In accordance with a related embodiment, the biotransformation is carried out under continuous agitation.

In accordance with an aspect, the present invention provides a process for producing galacto-oligosaccharides in high yield. In accordance with an embodiment, galacto-oligosaccharides yield is at least 80%, preferably 85%. The yield of galacto-oligosaccharides is calculated by the following formula:

Galacto-oligosaccharides yield (%)=galacto-oligosaccharides formed/total sugars×100

In accordance with an embodiment, the bioreactor is aerobic bioreactor. The aeration flow ranges from 0.1 to 1 vvm. In accordance with an aspect, the agitation speed ranges from 100 to 200 rpm. In accordance with an aspect, the agitation was 150 rpm during biotransformation in a 50 L bioreactor.

In accordance with an aspect of the invention, the pH of biotransformation medium in bioreactor ranges from 3.0 to 5.0. In accordance with an aspect, the biotransformation medium does not require pH adjustment.

In accordance with an embodiment of the invention, filtering of the galacto-oligosaccharides is carried out by any of the known means but not limited to, microfiltration, nanofiltration, resin column, chromatographic separation, simulated moving bed separation, centrifugation charcoal treatment and combination thereof. Separation is carried out to separate galacto-oligosaccharides from byproducts and colour and other impurities generated as a result of biotransformation process. Filtration, microfiltration and nanofiltration allow separating the microbes from remaining broth and galacto-oligosaccharides. Charcoal treatment removes color and organic impurities present in the produced galacto-oligosaccharides. In accordance with an aspect, the content of the galacto-oligosaccharides is more than 85%.

In accordance with an embodiment, harvested microbes are reused in more than one cycle for biotransformation. In accordance with an aspect, the microbes do not significantly lose its biotransformation efficiency while used in recycling. In accordance with a preferred embodiment, the harvested microbes are reused in more than 10 cycles of biotransformation.

In accordance with an optional embodiment of the invention, the filtered galacto-oligosaccharides are made into powder form. In accordance with an aspect, any known method can be used to make the powder form but limited to spray drying and crystallization.

Example 1: Fermentation *Sporobolomyces singularis* for Producing Biomass at 50 L Scale 2 liters of enriched medium was prepared by adding 10.0 gm peptone, 6.0 gm yeast extract, 6.0 gm malt extract, 10.0 gm glucose anhydrous, 50 gm lactose, 1.0 gm magnesium sulfate, 0.02 gm ferrous sulphate (Iron II sulfate) and pH of the medium was set at 6.5. The medium was sterilized at 121° C. for 15 min. After sterilization, the medium was inoculated with 10% (v/v) of *Sporobolomyces singularis* MCC 0096 (isolated from the Pune, Maharashtra, India) culture and incubated under aerobic condition at 27±0.5° C. on a rotary shaker for a period 30 hours at 150-200 rpm. When $OD_{620}$ reaches to 2.3, 5% of inoculum was transferred into 50 L fermenter with 35 L of sterile medium containing 5.0 g/l peptone, 3.0 g/l yeast extract, 3.0 g/l malt extract, 5.0 g/l glucose anhydrous, 25 g/l lactose, 0.5 g/l magnesium sulfate, 0.01 g/l ferrous sulphate (Iron II sulphate). The pH of the medium was set at pH 6.5. The inoculated media was incubated at 27±0.5° C. for the period of 48 hours at 350 rpm of agitation and 1 vvm of aeration.

Samples were drawn in sterile conditions after 24 hours at an interval of 6 hours and supernatant of culture was injected into HPLC to check the lactose utilization. The result of periodic lactose utilization is shown in table 1. The batch was harvested once the culture $OD_{620nm}$ reaches 5.5 after checking with colorimeter and maximum utilization of lactose and production of GOS as confirmed from HPLC. Harvested biomass was passed though membrane filtration and the concentrated biomass was centrifuged at 10000 rpm for 30 min. The obtained biomass was then utilized for biotransformation of lactose to produce GOS.

TABLE 1

Periodic lactose utilization

| S. No | Time | OD$_{620}$ | pH | Lactose % | GOS % |
|---|---|---|---|---|---|
| 1 | 0 | 0.2 | 6.13 | 100 | 0 |
| 2 | 24 | 1.6 | 5.9 | 100 | 0 |
| 3 | 36 | 3.5 | 5.81 | 75.9 | 24.1 |
| 4 | 39 | 4.3 | 5.63 | 61.4 | 38.6 |
| 5 | 42 | 4.8 | 5.2 | 44.8 | 55.2 |
| 6 | 45 | 5.4 | 5.07 | 30.5 | 69.5 |
| 7 | 48 | 5.6 | 5 | 20.9 | 79.1 |
| 8 | 52 | 5.6 | 4.8 | 18.7 | 81.3 |

Example 2: Biotransformation

25% of lactose solution (w/v) was prepared in distilled water in 50 L bioreactor by initially dissolving lactose in 50% of the total required volume and later it was made up to the final working volume of 35 L with distilled water. 7% of *Sporobolomyces singularis* biomass (w/v) was mixed with the prepared lactose solution uniformly until a homogenous suspension was formed. Biotransformation was carried out at a temperature of 37° C. The aeration was kept at 0.5 vvm and agitation at 150 rpm. Samples were taken at regular intervals, centrifuged at 10,000 rpm for 10 minute and cell free supernatant was analyzed by HPLC. When GOS content reached between 80-85%, the reaction mixture was passed though cross flow microfiltration system to withdraw half of the volume of cell free GOS from the permeate line and half of the volume of reaction mixture retained in the bioreactor. Fresh 25% (w/v) of lactose solution (18 Lit) was prepared and added with the half volume of reaction mixture in the bioreactor to start the next cycle batch. After every 3 cycles, 2% (w/v) of additional biomass was added to the reaction mixture for continuing the reaction to maintain the higher levels of GOS. The cycles were continued with the same biomass until there was 10% drop in content of GOS. The experiment was conducted for 10 cycles and GOS yield data has been represented in FIG. 2.

Example 3: Analysis of GOS and Determination of Sugar Composition by HPLC

The amount of GOS and other saccharides produced were analyzed using JASCO high performance liquid chromatography (HPLC) equipped with Refractive Index detector. The samples were filtered through 0.2µ membrane and 10 µL samples were injected into Asahipak NH$_2$P-50 4E (Shodex) column. Mobile phase was 75% (v/v) Acetonitrile and 25% Water with a flow rate of 1.5 mL/minute and column temperature was maintained at 30° C. Glucose and galactose were used as monosaccharide standards and lactose was used as a disaccharide standard. The quantitative analysis of GOS in samples was determined by the percentage area distribution of di-, tri-, tetra- and penta-saccharides and Degree of polymerization (DP) of oligosaccharide was calculated using their respective retention time.

Example 4: Identification of GOS Components by AOAC Method

GOS was identified based on AOAC 2001.02 using β-galactosidase enzyme treatment, which hydrolyses GOS into glucose and galactose. In this method, 10 Brix GOS test sample was injected in HPLC RI system to know the initial concentration of each analyte. After this, β-galactosidase enzyme was added to the test sample at a concentration of 10 mg/ml. Sample was incubated in shaker at 37° C. and 120 rpm for 3 hours. Enzyme was inactivated by heating the sample in boiling water bath for 10 min. After inactivation of enzyme, sample was centrifuged, filtered and injected in HPLC RI to measure the increase of glucose and galactose concentration. The analyte peaks were quantified against standard analyte peaks.

FIG. 3 shows the HPLC chromatogram profile of 3$^{rd}$ cycle of biotransformation. Number 1 represents galactose and glucose, 2 represents disaccharides, 3 represents lactose, 4 represents trisaccharides I, 5 represents 4-galactosyl lactose, 6 represents tetrasaccharides I, and 7 represents tetragsaccharides II.

Example 5: Standardization of Temperature During Biotransformation for Production of GOS To study the effect of temperature on GOS production during biotransformation, 25% (w/v) Lactose solution was prepared in distilled water. Cell biomass of *Sporobolomyces singularis* (10% w/v) obtained from fermentation was suspended in 25% lactose solution and volume was made up to 100 mL homogenous suspension in 500 mL Erlenmeyer flask. Reaction mixture was incubated at different temperatures ranging from 30, 33, 35 and 37° C. in Rotary Shaker at 125 rpm for 54 hr. After incubation, samples were analysed to check the lactose, glucose and GOS content by HPLC and have been tabulated in table 2.

TABLE 2

Temperature effect on biotransformation

| Temp. | Hours | 24 | 36 | 46 | 54 |
|---|---|---|---|---|---|
| 30° C. | GOS (%) | 32.34 | 40.94 | 47.53 | 56.02 |
|  | Remaining Lactose (%) | 59.39 | 48.3 | 40.46 | 29.71 |
|  | Others (%) | 8.28 | 10.74 | 12.01 | 13.28 |
| 33° C. | GOS (%) | 39.69 | 45.23 | 50.86 | 60.44 |
|  | Remaining Lactose (%) | 50.19 | 43.4 | 42.8 | 36.23 |
|  | Others (%) | 10.13 | 11.37 | 6.35 | 3.33 |
| 35° C. | GOS (%) | 41.14 | 51.56 | 73.25 | 85.85 |
|  | Remaining Lactose (%) | 46.88 | 38.33 | 24.79 | 9.06 |
|  | Others (%) | 11.98 | 10.11 | 1.97 | 5.10 |
| 37° C. | GOS (%) | 39.76 | 54.33 | 76.12 | 87.46 |
|  | Remaining Lactose (%) | 48.98 | 39.06 | 21.13 | 9.22 |
|  | Others (%) | 11.26 | 6.61 | 2.75 | 6.29 |

Example 6: Downstream Processing

The product obtained after biotransformation was cooled, treated with charcoal 0.3%, incubated for 4 hours under stirring and filtered through activated carbon pad to remove colour. The charcoal treated clear solution was then passed through cation exchange resin (Thermax—T52HUPS), followed by anion exchange resin (Thermax—Tulsion A3601) to remove the impurities and salts (Na, Ca, K etc.) present in the product. The resin passed GOS solution was filtered through 0.2µ filter pad, followed by concentration at 40° C. under vacuum to obtain syrup of 75% with dissolved solid content of ≥85% GOS.

INDUSTRIAL APPLICABILITY

The process as disclosed allows for production of high yield and high purity galacto-oligosaccharides in a simple and efficient manner. The process uses microbial cell, is easy to carry out and is of low cost. Moreover, the process disclosed excludes costly and time consuming downstream process requirement for removal of unwanted sugars.

Galacto-oligosaccharides, belongs to the group of prebiotics. Prebiotics are defined as non-digestible food ingredients that beneficially affect the host by stimulating the growth and/or activity of beneficial bacteria in the colon. Galacto-oligosaccharides occur in commercially available products such as food for both infants and adults.

The embodiments described above are only descriptions of preferred embodiments of the present invention, and do not intended to limit the scope of the present invention. Various variations and modifications can be made to the technical solution of the present invention by those of ordinary skills in the art, without departing from the design and spirit of the present invention. The variations and modifications should all fall within the claimed scope defined by the claims of the present invention.

What is claimed is:

1. A process for producing galacto-oligosaccharides comprising:
   (a) growing *Sporobolomyces singularis* MCC 0096 microbes in a fermentation medium;
   (b) harvesting the microbes;
   (c) inoculating the harvested microbes with lactose solution in a reactor in an aerobic condition, at a temperature in the range of 35 to 40° C., wherein the ratio of the said microbes with respect to lactose solution is at least 5% on w/v basis;
   (d) separating the galacto-oligosaccharides from the microbes;
   (e) filtering the obtained galacto-oligosaccharides of step (d);
   (f) optionally making a powder form of galacto-oligosaccharides, wherein the microbes convert at least 80% of lactose into galacto-oligosaccharides.

2. The process of claim 1, wherein the microbes are harvested from the fermentation medium at the $OD_{620}$ range of 5.0-6.0.

3. The process of claim 1, wherein microbes are grown in the fermentation medium at a temperature range of 25 to 30° C. in an aerobic condition.

4. The process of claim 1, wherein the separation is carried out using a microfiltration system and/or centrifugation.

5. The process of claim 1, wherein the powder is made by at least one of spray drying and crystallization.

6. The process of claim 1, wherein the yield of galacto-oligosaccharides is at least 80%.

7. The process of claim 1, wherein the microbes are reused.

* * * * *